(12) United States Patent
Umeda et al.

(10) Patent No.: US 9,921,195 B2
(45) Date of Patent: Mar. 20, 2018

(54) LIQUID CHROMATOGRAPHY-MASS SPECTROMETRY DEVICE

(71) Applicant: Hitachi High-Technologies Corporation, Minato-ku, Tokyo (JP)

(72) Inventors: Mitsuhiro Umeda, Tokyo (JP); Shinji Yoshioka, Tokyo (JP); Masaki Yoshie, Tokyo (JP); Yasushi Terui, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/110,028

(22) PCT Filed: Dec. 5, 2014

(86) PCT No.: PCT/JP2014/082189
§ 371 (c)(1),
(2) Date: Jul. 6, 2016

(87) PCT Pub. No.: WO2015/111311
PCT Pub. Date: Jul. 30, 2015

(65) Prior Publication Data
US 2016/0327527 A1 Nov. 10, 2016

(30) Foreign Application Priority Data
Jan. 27, 2014 (JP) .................................. 2014-012077

(51) Int. Cl.
*H01J 49/00* (2006.01)
*G01N 30/72* (2006.01)
(Continued)

(52) U.S. Cl.
CPC .......... *G01N 30/7266* (2013.01); *H01J 49/06* (2013.01); *H01J 49/061* (2013.01); *H01J 49/165* (2013.01); *H01J 49/24* (2013.01)

(58) Field of Classification Search
CPC .... G01N 30/7266; H01J 49/24; H01J 49/165; H01J 49/061; H01J 49/06
USPC ......................................... 250/281, 282, 288
See application file for complete search history.

(56) References Cited

U.S. PATENT DOCUMENTS 6,815,667 B2 11/2004 Tanner et al.
8,227,750 B1 7/2012 Zhu et al.
(Continued)

FOREIGN PATENT DOCUMENTS

JP 2000-357488 A 12/2000
JP 2004-507875 A 3/2004
(Continued)

OTHER PUBLICATIONS

Japanese-language Office Action issued in counterpart Japanese Application No. 2015-558748 dated Mar. 7, 2017 with English translation (Twelve (12) pages).
(Continued)

*Primary Examiner* — Michael Maskell
(74) *Attorney, Agent, or Firm* — Crowell & Moring LLP

(57) ABSTRACT

This invention improves the sensitivity of a liquid chromatography-mass spectrometry device by reducing the number of neutral particles that are not ionized during ionization and the number of low-molecular ions from a solvent used in the liquid chromatography. Said liquid chromatography-mass spectrometry device is provided with ion sources, a mass spectrometry unit, a detector, and three electrodes laid out so as to be parallel to each other. The first electrode and the second electrode have openings that allow ions to pass therethrough. The trajectories of said ions are deflected between the second electrode and the third electrode, thereby directing ions generated by the ion sources towards the mass spectrometry unit.

19 Claims, 5 Drawing Sheets

(51) Int. Cl.
*H01J 49/06* (2006.01)
*H01J 49/16* (2006.01)
*H01J 49/24* (2006.01)

(56) References Cited

U.S. PATENT DOCUMENTS

2002/0121599 A1* 9/2002 Kato .................. H01J 49/04
 250/288
2008/0067351 A1* 3/2008 Satoh .................. H01J 49/004
 250/287
2015/0021469 A1* 1/2015 Bajic .................. H01J 49/0454
 250/282

FOREIGN PATENT DOCUMENTS

JP 2004-303497 A 10/2004
JP 2007-287404 A 11/2007
WO WO 2013/093517 A1 6/2013

OTHER PUBLICATIONS

International Search Report (PCT/ISA/210) issued in PCT Application No. PCT/JP2014/082189 dated Jan. 13, 2015 with English-language translation (two (2) pages).
Japanese-language Written Opinion (PCT/ISA/237) issued in PCT Application No. PCT/JP2014/082189 dated Jan. 13, 2015 (three (3) pages).
Extended European Search Report issued in counterpart European Application No. 14880181.4 dated Aug. 21, 2017 (Seven (7) pages).
Nevado, et al., "Advantages of Using a Modified Orthogonal Sampling Configuration Originally Designed for LC-ESI-MS to Couple CE and MS for the Determination of Antioxidant Phenolic Compounds Found in Virgin Olive Oil," Talanta, vol. 82, No. 2, Jul. 15, 2010, pp. 548-554, XP027120451 (Seven (7) pages).

* cited by examiner

[FIG. 1]
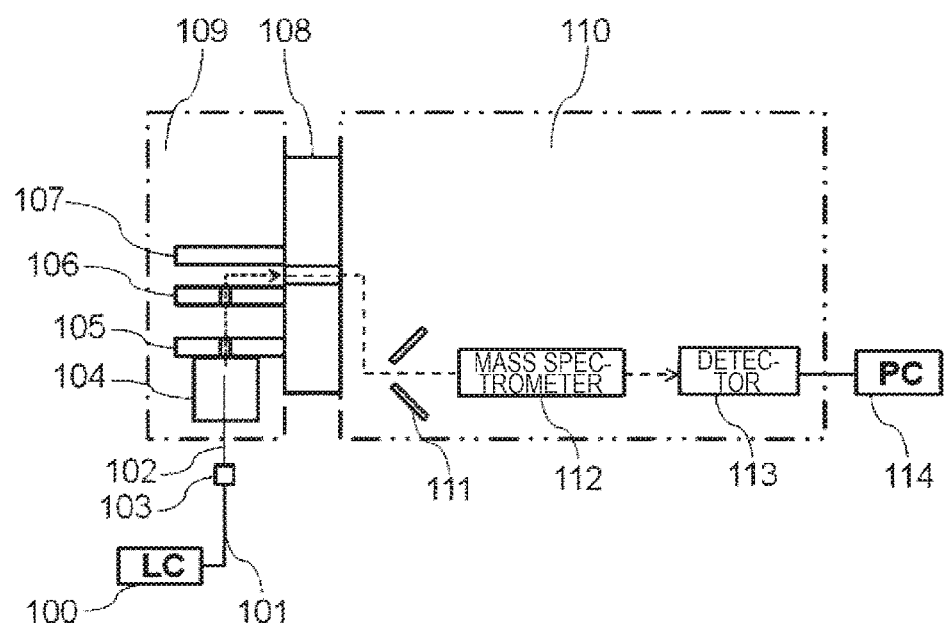

[FIG. 2]
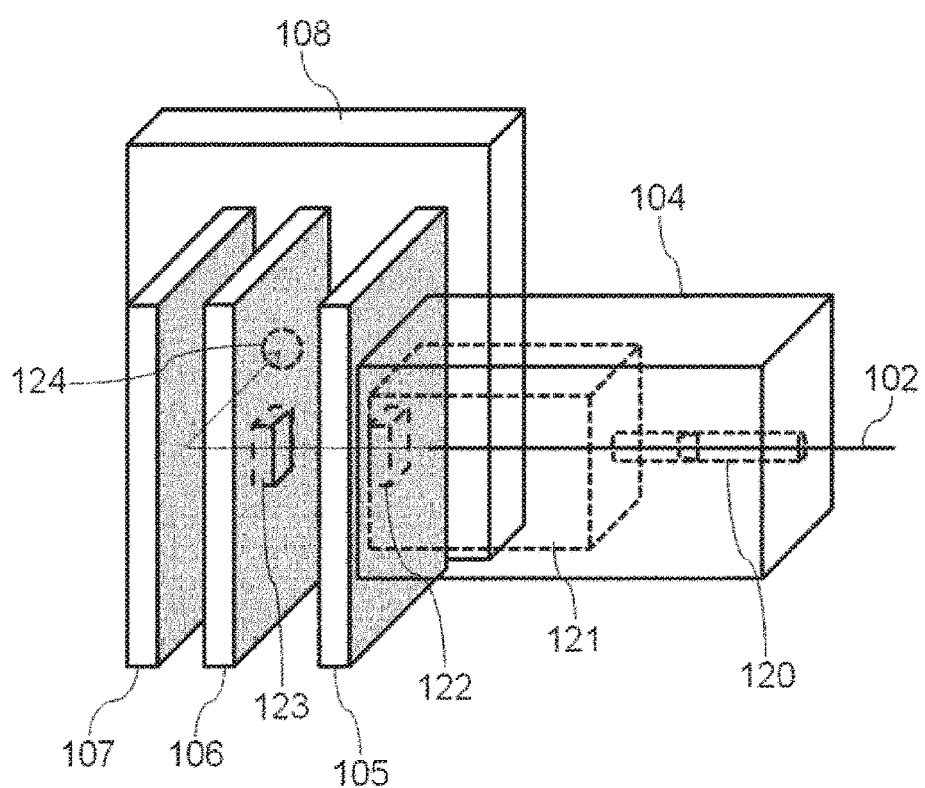

[FIG. 3]
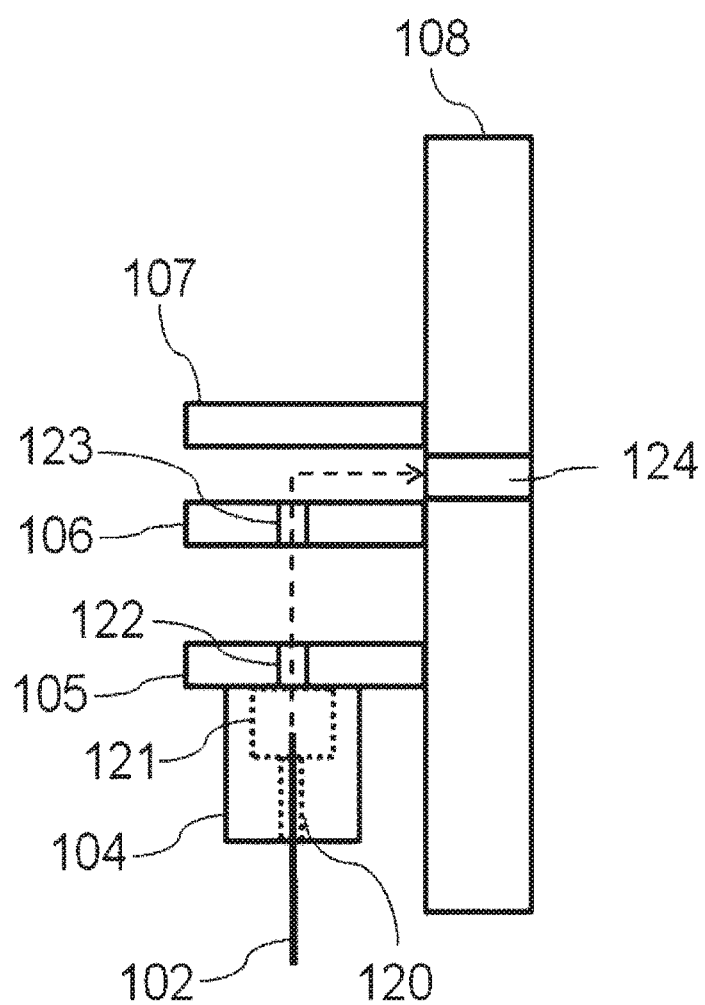

[FIG. 4]
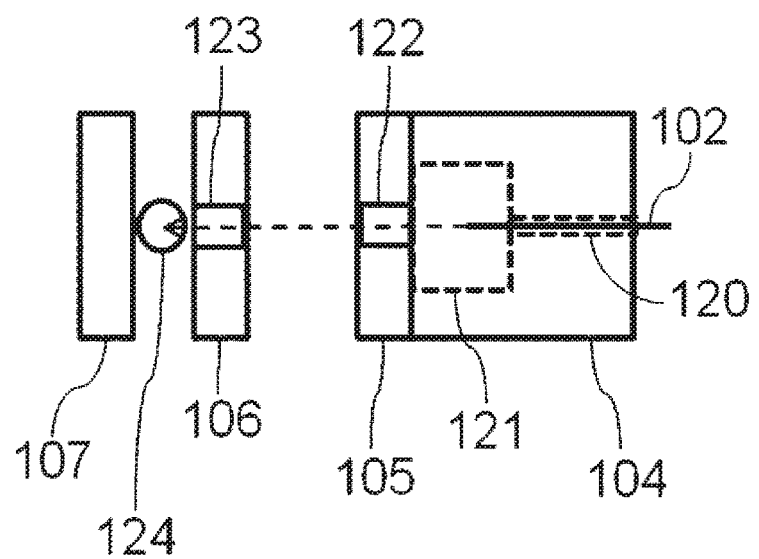

[FIG. 5]
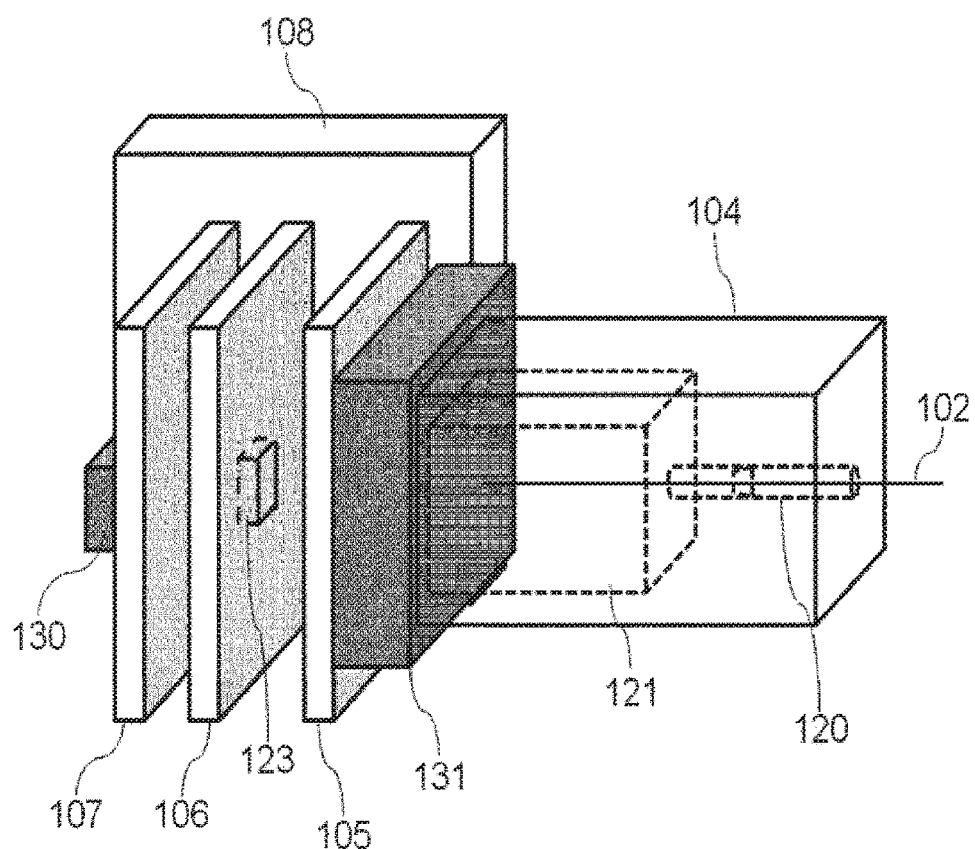

LIQUID CHROMATOGRAPHY-MASS SPECTROMETRY DEVICE

TECHNICAL FIELD

The present invention relates to a liquid chromatography-mass spectrometry device.

BACKGROUND ART

Recently, liquid chromatography-mass spectrometry devices are often used as highly sensitive means for obtaining qualitative/quantitative information on multiple components in minute amounts (order of ppm to ppb) in the fields of environment, food, pharmaceuticals, forensic medicine and the like. Thus, a device which is not only highly sensitive, which is one of the characteristics of mass spectrometry, but also simpler and highly durable and which requires simple maintenance only is desired.

One of the ionization techniques that are generally used at the interface between the liquid chromatograph and the mass spectrometer is an electrospray ion source (ESI) using the electrospray ionization technique. This is an ionization technique for generating ions by spraying a sample solution at atmospheric pressure, and one of the characteristics is that ions having information on molecular weights are generated selectively. In a liquid chromatography-mass spectrometry device using an electrospray ion source (ESI), the components in a sample mixture are separated by a liquid chromatograph, and ions are generated in an ionization unit at atmospheric pressure. Then, the ions enter a mass spectrometry unit through a first fine aperture or the like and separated according to the mass. A detection unit detects the ionic strengths, which are displayed as a mass spectrum and chromatogram data by a data processor. The types of the mass spectrometry device used in the mass spectrometry unit include a quadrupole mass spectrometer, an ion trap, a tandem quadrupole mass spectrometer, a time-of-flight mass spectrometer and the like. In general, the flow rate of the mobile phase solvent used for liquid chromatography is several hundred microliters per minute to several milliliters per minute. In order to increase the efficiency of evaporation of droplets of the sample solution sent from the liquid chromatograph and sprayed at such a high flow rate, there is a method in which heated dry gas such as N2 is blown on the droplets of the sprayed sample solution to facilitate the evaporation of the sample droplets. At this point, it is important that the droplets of the sample solution and the dry gas such as N2 are stirred thoroughly to sufficiently evaporate the droplets of the sample solution created by spraying. Accordingly, the structure for ionization becomes complex, and the ionization unit often has a large structure due to the use of gas at high temperature or the like. Because evaporation during ionization is difficult when the flow rate of the solution sent from the liquid chromatograph is high, the nano- and micro-electrospray ionization techniques in which ionization is conducted at a flow rate of several hundred nanoliters per minute to several microliters per minute for the purpose of obtaining high sensitivity are used recently. By reducing the amount of the sample sprayed and thus discharging and spraying the sample by small amounts, the use of the gas at high temperature, which is required for a high flow rate, and the ionization voltage can be reduced, and the ion source can be designed to have a small structure. However, to electrospray a sample at such a low flow rate, the opening at the end of the spraying portion has a small inner diameter of several dozen micrometers to 100 micrometers, and the opening is clogged with the sample. Thus, the spraying portion often requires frequent maintenance and replacement operations. Also, the positional relation with the inlet for the ions is important because of the small opening diameter, and it is required to adjust the positions to achieve good ionization state every time maintenance operations such as the replacement of the spraying portion are conducted. Accordingly, it is not possible yet to provide a simple, highly durable device which requires simple maintenance only which is required when the micro-electrospray ionization technique is used to increase the sensitivity.

There is a patent relating to the structure of an ion source for a low flow rate using the micro-electrospray ionization technique, as shown in PTL 1. There is a method in which the parts from the spraying portion where the sample is ionized to the fine aperture through which the ions enter the mass spectrometer are fixed in such a manner that the parts are aligned on a same line. In this method however, because the neutral molecules and the droplets in the sprayed sample solution that are not involved in the ionization are also sprayed towards the facing inlet for the ions, it is thought that there is influence of contamination on the surface of the inlet for the ions, contamination in the fine aperture and contamination in the vacuum chamber. It may be possible to increase the amount of the ions introduced, increase the signal intensities and ensure the stability by aligning the parts on a same line, but it is difficult to provide a highly durable mass spectrometer. Also, when the inside of the vacuum chamber is affected, it is required to stop creating the vacuum in the device to conduct maintenance.

CITATION LIST

Patent Literature

PTL 1: U.S. Pat. No. 8,227,750

SUMMARY OF INVENTION

Technical Problem

At the interface with the liquid chromatograph in a liquid chromatography-mass spectrometry device, the flow rate of the mobile phase solvent that is generally used for the liquid chromatograph is several hundred microliters per minute to several milliliters per minute. When a sample solvent sent at such a flow rate is sprayed, the sensitivity is improved for example by blowing dry gas such as N2 heated to high temperature on the droplets of the sprayed sample solution to facilitate the evaporation of the sample droplets. However, as the structure of the ion source becomes complex and large, a method in which the use of the gas at high temperature, which is required for a high flow rate, and the ionization voltage are reduced by reducing the flow rate of the sample introduced to the ion source to several hundred nanoliters per minute to several microliters per minute and thus discharging and spraying the sample by small amounts is used for high sensitivity measurement. However, to electrospray a sample at such a low flow rate, the opening at the end of the spraying portion has a small inner diameter of several dozen micrometers to 100 micrometers, and the opening is clogged with the sample. Thus, the spraying portion often requires frequent maintenance and replacement operations. Also, the positional relation with the inlet for the ions is important because of the small opening diameter of the spraying portion, and it is required to adjust the positions to achieve good ionization state every time maintenance operations such as the replacement of the spraying portion are conducted.

Also, from the viewpoint of a highly durable device which is required for a liquid chromatography-mass spectrometry device, noise is observed when ions derived from the solvent for the sample for introducing the sample sent from the liquid chromatograph to the mass spectrometry device or the uncharged neutral particles collide with the detector in the mass spectrometry device. When the solvent-derived ions or the neutral particles are introduced into the vacuum chamber and contaminate the ion lens system or the mass spectrometry unit in the vacuum, it is required to stop creating the vacuum to conduct maintenance, and it takes a long time to restart the device. Moreover, an expert knowledge is required for the maintenance. Thus, it has been desired that the pollution of the device is prevented at the atmospheric side (without stopping creating the vacuum).

Solution to Problem

The liquid chromatography-mass spectrometry device of the invention is a liquid chromatography-mass spectrometry device which can be coupled with liquid chromatography, having an ion source, a mass spectrometry unit and a detector and further having three electrodes disposed parallel to each other, wherein the first electrode and the second electrode each have an opening that allows ions to pass therethrough, and the trajectories of ions are deflected between the second electrode and the third electrode, thereby directing ions generated by the ion source towards the mass spectrometry unit.

Advantageous Effects of Invention

According to the invention, it is possible to provide a liquid chromatography-mass spectrometry device having a unit of ionization structures in which the end of the spraying portion in the ion source, the counter electrode, the front stage electrode and the subsequent stage electrode are aligned along a same axis, and the intermediate part between the front stage electrode and the subsequent stage electrode and the center of a fine aperture of the vacuum chamber introduction electrode are aligned along a same axis, in a micro-electrospray ion source (ESI) using the electrospray ionization technique. Due to this structure, the number of neutral particles that are not ionized during ionization and the number of low-molecular ions derived from the solvent used in the liquid chromatograph are reduced, and the sensitivity of the device is increased. At the same time, it is possible to achieve liquid chromatography-mass spectrometry using a micro-electrospray ion source (ESI) having the properties: the pollution caused when a liquid sample is measured by the mass spectrometry device can be separated and sorted at the atmospheric side; the maintenance of the device can be conducted in an atmospheric environment; the positioning of the spraying portion after the maintenance is more reproducible; and the settings of the ionization conditions after the maintenance operations by a user are easy.

BRIEF DESCRIPTION OF DRAWINGS

FIG. 1 An example of the structure of a mass spectrometry device according to the invention.

FIG. 2 Detailed structures from an ion source to a vacuum chamber introduction electrode according to the invention.

FIG. 3 A top view of detailed structures from the ion source to the vacuum chamber introduction electrode according to the invention.

FIG. 4 A side view of detailed structures from the ion source to the vacuum chamber introduction electrode according to the invention.

FIG. 5 Detailed structures from the ion source to the vacuum chamber introduction electrode according to the invention, a heater and heat insulation.

DESCRIPTION OF EMBODIMENTS

Examples of the invention are explained below referring to the drawings.

EXAMPLES

FIG. 1 is a schematic view of an example structure of the mass spectrometry device according to the invention. The sample solution sent (at 0.5 µL/min to 10 µL/min) from a liquid chromatograph 100 is introduced to a spray tip 102 through a tube 101. To generate ions by micro-electrospray ionization technique, the sample solution is subjected to a high voltage at a high voltage applying portion 103 and then introduced to the spray tip 102, where the sample solution is converted into a static droplet. The droplet is ionized as the volume thereof reduces. An ion source block 104 is at atmospheric pressure. The ions generated pass through a slit in a counter electrode 105 of a flat plate shape. The ions which have passed the counter electrode 105 pass through a slit in a front stage electrode 106 and enter the space between the front stage electrode 106 and a subsequent stage electrode 107. The front stage electrode 106 and the subsequent stage electrode 107 are disposed parallel to each other and have a flat plate shape like the counter electrode 105. The ions are deflected between the front stage electrode 106 and the subsequent stage electrode 107 and travel towards a vacuum chamber introduction electrode 108. The vacuum chamber introduction electrode 108 functions as a vacuum partition between an atmospheric pressure chamber 109 and a vacuum chamber 110. The ions enter the vacuum chamber 110 through a fine aperture in the vacuum chamber introduction electrode 108. The ions pass through a fine aperture 111 in the vacuum chamber 110 and are mass analyzed by a mass spectrometer 112. The ions are detected by a detector 113, and the data are obtained by a PC 114. The PC 114 obtains the data and also controls the device.

FIG. 2 shows details from the ion source block 104 to the vacuum chamber introduction electrode 108. A tip-fixing portion 120 for fixing the spray tip 102 and a cavity 121 are provided inside the ion source block 104. The spray tip 102 is fixed with the tip-fixing portion 120, and the end of the spray tip 102 is located in the cavity 121. The ion source block 104 is placed closely and perpendicularly to the counter electrode 105 in such a manner that the center of the tip-fixing portion 120 and the center of a slit 122 in the counter electrode are aligned along a same axis. As a result, the spray tip 102 fixed with the tip-fixing portion 120 is aligned along the same axis as the center of the slit 122 in the counter electrode, and the ions can pass through the center of the slit 122 in the counter electrode.

Also, regarding the counter electrode 105, the front stage electrode 106 and the subsequent stage electrode 107, these three electrodes are disposed parallel to each other and perpendicularly to the vacuum chamber introduction electrode 108. In this regard, by forming a slit of the same shape to pass the ions through in the front stage electrode 106 as in the counter electrode 105, the center of the slit 122 in the counter electrode and the center of a slit 123 in the front stage electrode are aligned along a same axis. This configuration allows the ions generated by micro-electrospray ionization technique at the spray tip 102 to enter the space between the front stage electrode 106 and the subsequent stage electrode 107 efficiently. In this regard, the device may also have the ability to separate the ions according to the ion mobilities in the space using the two parallel plates, namely, the front stage electrode 106 and the subsequent stage electrode 107.

Subsequently, the ions pass the vacuum chamber introduction electrode 108 due to the potential difference between the front stage electrode 106 and the subsequent stage electrode 107 and enter the vacuum chamber 110.

FIG. 3 is a top view of the details from the ion source block 104 to the vacuum chamber introduction electrode 108. FIG. 4 is a side view of the details from the ion source block 104 to a fine aperture 124 in the vacuum chamber introduction electrode. The ions which have passed the center of the front stage electrode 106 turn at a right angle between the front stage electrode 106 and the subsequent stage electrode 107 and travel towards the vacuum chamber introduction electrode 108. The front stage electrode 106 and the subsequent stage electrode 107 are placed closely and perpendicularly to the vacuum chamber introduction electrode 108 in such a manner that the middle point between the front stage electrode 106 and the subsequent stage electrode 107 and the center of the fine aperture 124 in the vacuum chamber introduction electrode are aligned along a same axis. This configuration allows the ions to pass through the center of the fine aperture 124 in the vacuum chamber introduction electrode efficiently after turning between the front stage electrode 106 and the subsequent stage electrode 107.

The slit 122 in the counter electrode and the slit 123 in the front stage electrode, through which the ions pass, each have a width of about 0.5 mm and a length of about 5 mm, and the fine aperture 124 in the vacuum chamber introduction electrode has an inner diameter of about 0.4 mm. To obtain sufficient sensitivity, the end of the spray tip 102 is within about ±0.2 mm horizontally and within about ±1.5 mm vertically from the center of the slit 122 in the counter electrode, and the distance from the slit is adjustable depending on the flow rate of the sample introduced to the spray tip 102 and should be able to be adjusted within 15 mm. Accordingly, the accuracy of the positioning of the slits and the fine aperture is important for good ionization state. Also, the slits in the counter electrode 105 and the front stage electrode 106 may have a circular shape with an inner diameter of 2 to 4 mm. In this structure, the end of the spray tip 102 in the ion source block 104, the counter electrode 105, the front stage electrode 106 and the subsequent stage electrode 107 are aligned along a same axis and the intermediate part between the front stage electrode 106 and the subsequent stage electrode 107 and the center of the fine aperture 124 in the vacuum chamber introduction electrode are aligned along a same axis, and thus the positions are maintained accurately. The ions generated can be thus introduced to the vacuum chamber 110 efficiently.

In this structure, to improve the robustness, a mechanism for introducing nitrogen gas to the space between the counter electrode 105 and the front stage electrode 106 is provided. With this mechanism, the neutral molecules, the droplets and the like that are not involved in the ionization are prevented from reaching the electrodes beyond the counter electrode 105. The ions generated turn at a right angle between the front stage electrode 106 and the subsequent stage electrode 107 and enter the vacuum chamber 110. The neutral molecules, the droplets and the like that are not involved in the ionization cannot pass through the space between the front stage electrode 106 and the subsequent stage electrode 107 and thus cannot pass the vacuum chamber introduction electrode 108. Therefore, the contamination of the vacuum chamber 110 can be reduced, and the robustness of the mass spectrometer improves.

Also, by designing the ion source block 104, the counter electrode 105, the front stage electrode 106, the subsequent stage electrode 107 and the vacuum chamber introduction electrode 108 as a unit structure, the positioning of the electrodes and the ion source block 104 when attaching them again after removing them for the maintenance operations is more reproducible, and the adjustment of the positions for good ionization state is not necessary.

FIG. 5 is a figure in which a heater 130 and a heat insulator 131 have been added to FIG. 2 showing the details from the ion source block 104 to the vacuum chamber introduction electrode 108. To obtain an effect of removing the solvent from the sample solvent sprayed from the spray tip 102 in the ion source block 104, the counter electrode 105, the front stage electrode 106 and the subsequent stage electrode 107 are heated with the heat of the heater 130. At this point, bumping of the sample solvent introduced from the liquid chromatograph may occur when the ion source block 104 and the spray tip 102 are similarly heated to high temperature. Thus, the temperature should be 70° C. or lower to prevent the bumping of the sample solvent. Accordingly, by interposing the heat insulator 131 between the ion source block 104 and the counter electrode 105, a temperature gradient can be created between the portion including the three electrodes, namely the counter electrode 105, the front stage electrode 106 and the subsequent stage electrode 107, and the spraying portion including the ion source block 104 and the spray tip 102. As a result, the bumping of the sample solvent can be prevented, and stable ionization with high sensitivity can be achieved.

REFERENCE SIGNS LIST

100 Liquid chromatograph
101 Tube
102 Spray tip
103 High voltage applying portion
104 Ion source block
105 Counter electrode
106 Front stage electrode
107 Subsequent stage electrode
108 Vacuum chamber introduction electrode
109 Atmospheric pressure chamber
110 Vacuum chamber
111 Fine aperture
112 Mass spectrometer
113 Detector
114 PC
120 Tip-fixing portion
121 Cavity
122 Slit in counter electrode
123 Slit in front stage electrode
124 Fine aperture in vacuum chamber introduction electrode
130 Heater
131 Heat insulator

The invention claimed is:

1. A liquid chromatography-mass spectrometry device which can be coupled with liquid chromatography,
having an ion source, a mass spectrometry unit and a detector,
further having three electrodes disposed parallel to each other,
characterized in that the first electrode and the second electrode each have an opening that allows ions to pass therethrough, and
the trajectories of ions are deflected between the second electrode and the third electrode, thereby directing ions generated by the ion source towards the mass spectrometry unit, wherein the liquid chromatography-mass spectrometry device further has a heating unit for heating the three electrodes.

2. The liquid chromatography-mass spectrometry device according to claim 1,
characterized in that the openings in the first electrode and the second electrode have a circular shape.

3. The liquid chromatography-mass spectrometry device according to claim 1,
wherein the ions are separated according to the ion mobilities using the second electrode and the third electrode in the space between the second electrode and the third electrode.

4. The liquid chromatography-mass spectrometry device according to claim 1,
wherein the ion source has a high voltage applying unit, a spray tip and an ion source block, and
a heat insulator is disposed between the first electrode and the ion source block.

5. The liquid chromatography-mass spectrometry device according to claim 4,
wherein the end of the spray tip and the openings in the first electrode and the second electrode are aligned along a same axis.

6. The liquid chromatography-mass spectrometry device according to claim 1,
wherein the three electrodes are at atmospheric pressure.

7. The liquid chromatography-mass spectrometry device according to claim 1,
further having a vacuum chamber introduction electrode for introducing the ions to the mass spectrometry unit after the deflection between the second electrode and the third electrode.

8. The liquid chromatography-mass spectrometry device according to claim 7,
wherein the middle point between the second electrode and the third electrode and the center of the vacuum chamber introduction electrode are aligned along a same axis.

9. The liquid chromatography-mass spectrometry device according to claim 4,
wherein the end of the spray tip and the openings in the first electrode and the second electrode are aligned along a same axis,
a vacuum chamber introduction electrode for introducing the ions to the mass spectrometry unit after the deflection between the second electrode and the third electrode is provided,
the middle point between the second electrode and the third electrode and the center of the vacuum chamber introduction electrode are aligned along a same axis, and
the axis connecting the end of the spray tip and the openings in the first electrode and the second electrode intersect with the axis connecting the middle point between the second electrode and the third electrode and the center of the vacuum chamber introduction electrode.

10. The liquid chromatography-mass spectrometry device according to claim 7,
wherein the ion source has a high voltage applying unit, a spray tip and an ion source block, and
the ion source block, the first electrode, the second electrode and the third electrode are attachable and removable as a unit.

11. The liquid chromatography-mass spectrometry device according to claim 1,
wherein the ion source has a high voltage applying unit, a spray tip and an ion source block, and
the heating unit also heats the ion source block.

12. A liquid chromatography-mass spectrometry device which can be coupled with liquid chromatography,
having an ion source, a mass spectrometry unit and a detector,
further having three electrodes at atmospheric pressure and disposed parallel to each other,
characterized in that the first electrode and the second electrode each have an opening that allows ions to pass therethrough, and
the trajectories of ions are deflected between the second electrode and the third electrode, thereby directing ions generated by the ion source towards the mass spectrometry unit.

13. The liquid chromatography-mass spectrometry device according to claim 12,
characterized in that the openings in the first electrode and the second electrode have a circular shape.

14. The liquid chromatography-mass spectrometry device according to claim 12,
wherein the ions are separated according to the ion mobilities using the second electrode and the third electrode in the space between the second electrode and the third electrode.

15. The liquid chromatography-mass spectrometry device according to claim 12,
further having a heating unit for heating the three electrodes.

16. The liquid chromatography-mass spectrometry device according to claim 15,
wherein the ion source has a high voltage applying unit, a spray tip and an ion source block, and
a heat insulator is disposed between the first electrode and the ion source block.

17. The liquid chromatography-mass spectrometry device according to claim 16,
wherein the end of the spray tip and the openings in the first electrode and the second electrode are aligned along a same axis.

18. The liquid chromatography-mass spectrometry device according to claim 16,
wherein the ion source has a high voltage applying unit, a spray tip and an ion source block, and
the ion source block, the first electrode, the second electrode and the third electrode are attachable and removable as a unit.

19. The liquid chromatography-mass spectrometry device according to claim 15, wherein the ion source has a high voltage applying unit, a spray tip and an ion source block, and the heating unit also heats the ion source block.

* * * * *